(12) United States Patent
Verbeke et al.

(10) Patent No.: US 9,505,871 B2
(45) Date of Patent: Nov. 29, 2016

(54) ISOCYANATE-CONTAINING PREPOLYMER AND METHOD FOR MAKING THE SAME

(71) Applicant: Huntsman International LLC, The Woodlands, TX (US)

(72) Inventors: Wesley Verbeke, Steenokkerzeel (BE); Dimitri Leroy, Brussels (BE)

(73) Assignee: Huntsman International LLC, The Woodlands, TX (US)

( * ) Notice: Subject to any disclaimer, the term of this patent is extended or adjusted under 35 U.S.C. 154(b) by 0 days.

(21) Appl. No.: 14/380,734

(22) PCT Filed: Mar. 19, 2013

(86) PCT No.: PCT/EP2013/055658
§ 371 (c)(1),
(2) Date: Aug. 25, 2014

(87) PCT Pub. No.: WO2013/143915
PCT Pub. Date: Oct. 3, 2013

(65) Prior Publication Data
US 2015/0018508 A1    Jan. 15, 2015

(30) Foreign Application Priority Data

Mar. 29, 2012  (EP) .................................... 12162092

(51) Int. Cl.
| | |
|---|---|
| *C08G 18/28* | (2006.01) |
| *C09J 175/04* | (2006.01) |
| *C09J 175/06* | (2006.01) |
| *C07C 275/28* | (2006.01) |
| *C07C 275/04* | (2006.01) |
| *C07C 269/02* | (2006.01) |
| *C07C 271/28* | (2006.01) |
| *C07C 271/10* | (2006.01) |
| *C08G 18/10* | (2006.01) |
| *C08G 18/12* | (2006.01) |
| *C08G 18/76* | (2006.01) |
| *C08G 18/34* | (2006.01) |
| *C08G 18/18* | (2006.01) |

(52) U.S. Cl.
CPC ......... *C08G 18/2815* (2013.01); *C07C 269/02* (2013.01); *C07C 271/10* (2013.01); *C07C 271/28* (2013.01); *C07C 275/04* (2013.01); *C07C 275/28* (2013.01); *C08G 18/10* (2013.01); *C08G 18/12* (2013.01); *C08G 18/18* (2013.01); *C08G 18/1825* (2013.01); *C08G 18/282* (2013.01); *C08G 18/284* (2013.01); *C08G 18/288* (2013.01); *C08G 18/2825* (2013.01); *C08G 18/2865* (2013.01); *C08G 18/34* (2013.01); *C08G 18/7614* (2013.01); *C08G 18/7664* (2013.01); *C08G 18/7671* (2013.01); *C09J 175/04* (2013.01); *C09J 175/06* (2013.01); *C08G 2170/20* (2013.01)

(58) Field of Classification Search
CPC . C07C 269/02; C07C 271/10; C07C 271/28; C07C 275/04; C07C 275/28; C09J 175/04; C09J 175/06; C08G 2170/20; C08G 18/10; C08G 18/12; C08G 18/2815; C08G 18/282; C08G 18/2825; C08G 18/284; C08G 18/2865; C08G 18/288; C08G 18/7664; C08G 18/7671
See application file for complete search history.

(56) References Cited

U.S. PATENT DOCUMENTS

| | | | |
|---|---|---|---|
| 3,947,338 | A | 3/1976 | Jerabek et al. |
| 5,783,652 | A | 7/1998 | Rosthauser et al. |
| 5,880,167 | A | 3/1999 | Krebs et al. |
| 6,664,414 | B2 | 12/2003 | Tong et al. |
| 6,730,405 | B2 | 5/2004 | Bernard et al. |
| 2008/0214774 | A1 | 9/2008 | Brown et al. |
| 2009/0030161 | A1 | 1/2009 | Johnston et al. |
| 2010/0152381 | A1 | 6/2010 | Savino et al. |
| 2011/0015292 | A1 | 1/2011 | Radhakrishnan et al. |

FOREIGN PATENT DOCUMENTS

| | | |
|---|---|---|
| EP | 1188779 | 3/2002 |
| GB | 1450414 | 9/1976 |
| WO | 2009/144280 | 12/2009 |

OTHER PUBLICATIONS

Oertel; Polyurethane Handbook: Chemistry—Raw Materials—Processing—Applications—Properties; Hanser Publishers; New York; 1985; pp. 20 and 21.*

* cited by examiner

*Primary Examiner* — Rabon Sergent
(74) *Attorney, Agent, or Firm* — Robert A. Diaz

(57) ABSTRACT

The invention relates to an isocyanate-containing prepolymer obtainable by reacting at least one isocyanate with at least one first compound selected from the group comprising monohydric alcohols, thiols and secondary amines; wherein the ratio of the NCO value of the isocyanate-containing prepolymer, to the OH, SH or NH value, of said monohydric alcohol, thiol or secondary amine respectively ranges from 0.0005 to 1.0000 and wherein said at least one first compound is present in a total amount of at least 40% by weight based on the total weight of the isocyanate-containing prepolymer.

12 Claims, 1 Drawing Sheet

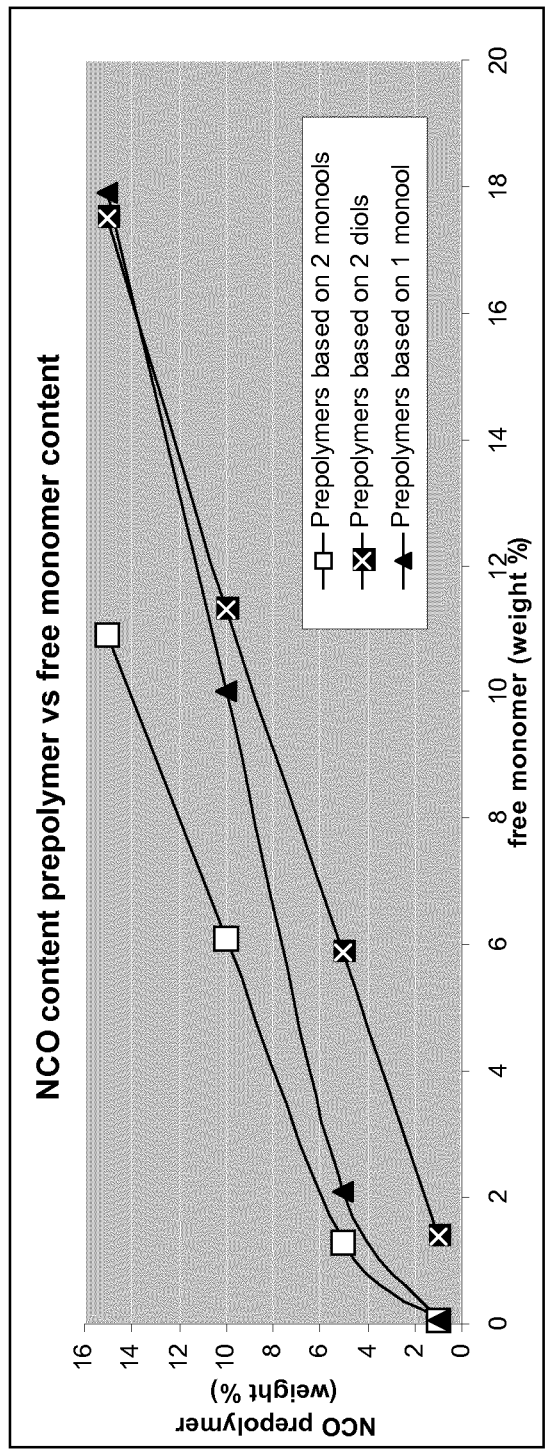

ISOCYANATE-CONTAINING PREPOLYMER AND METHOD FOR MAKING THE SAME

This application is the National Phase of International Application PCT/EP2013/055658 filed Mar. 19, 2013 which designated the U.S. and which claims priority to Foreign Application No. 12162092.6 filed Mar. 29, 2012. The noted applications are incorporated herein by reference.

FIELD OF THE INVENTION

The present invention relates to isocyanate-based prepolymers and uses thereof.

BACKGROUND TO THE INVENTION

Prepolymers bearing isocyanate groups are commonly used in industry to make a wide variety of polyurethane products. These prepolymers are usually prepared by reacting a polyol with an excess of a monomeric polyisocyanate, for example, a diisocyanate such as methylene diphenyl diisocyanate (MDI). Disadvantages associated with the process for forming these prepolymers, involve the unreacted monomers.

In the art, several methods exist to reduce free monomer content in prepolymers. Monomers can be stripped by distillation, more in particular for higher vapor pressure diisocyanate based prepolymers. Methylene diphenyl diisocyanates, on the other hand, have very low vapor pressures. Furthermore, vapor pressure is proportional to concentration. This combination makes it extremely difficult to remove methylene diphenyl diisocyanate monomers from prepolymers down to extremely low levels. In addition, the temperature during distillation is preferably not raised above 220° C., since MDI may start to form carbodiimides and $CO_2$. This process is expensive, requires high cost equipment, and a high investment for low vacuum pumps.

Alternatively, free monomer content can be reduced by asymmetric prepolymerization. However, as a result, the reactivity and curing behavior with water can be extremely low due to the full 2,4-isomer content. The mechanical properties for such prepolymers are less desirable as well. Additionally, raw material availability and price may be an issue.

Therefore, there remains a need for prepolymers and processes to prepare said prepolymers that overcome one or more of the aforementioned issues. It is an object of the present invention to overcome one or more of the aforementioned issues. More in particular, it is an object of the present invention to reduce free monomer content in prepolymers. More in particular, it is an object of the present invention to reduce free monomer content in prepolymers, while keeping good processability thanks to low viscosity. More in particular, it is an object of the present invention to reduce free monomer content in prepolymers, while keeping good mechanical properties. More in particular, it is an object of the present invention to reduce free monomer content in prepolymers, while keeping good processability thanks to low viscosity and good mechanical properties.

SUMMARY OF THE INVENTION

The present inventors have now surprisingly found that one or more of these objects can be obtained by mixing or reacting at least one monohydric alcohol, thiol or secondary amine at a selected concentration with an isocyanate.

According to a first aspect of the present invention, an isocyanate-containing prepolymer is provided, said prepolymer being obtainable by reacting at least one isocyanate with at least one first compound selected from the group comprising monohydric alcohols, thiols and secondary amines; wherein the ratio of the NCO value of the isocyanate-containing prepolymer to the OH, SH or NH value of said monohydric alcohol, thiol or secondary amine respectively ranges from 0.0005 to 1.0000, preferably from 0.0005 to 0.7500, preferably from 0.001 to 0.600 and wherein said at least one first compound is present in a total amount of at least 40% by weight based on the total weight of the isocyanate-containing prepolymer.

According to a second aspect, the present invention also encompasses a process for preparing an isocyanate-containing prepolymer according to the first aspect of the invention, comprising the step of:

(a) reacting at least one isocyanate with at least one first compound selected from the group comprising monohydric alcohols, thiols and secondary amines; wherein the ratio of the NCO value of the isocyanate-containing prepolymer to the OH, SH or NH value of said monohydric alcohol, thiol or secondary amine respectively ranges from 0.0005 to 1.0000, preferably from 0.0005 to 0.7500; preferably from 0.001 to 0.600 and wherein said at least one first compound is present in a total amount of at least 40% by weight based on the total weight of the isocyanate-containing prepolymer;

thereby preparing an isocyanate-containing prepolymer.

According to a third aspect, the invention encompasses a polyisocyanate composition comprising the isocyanate-containing prepolymer according to the first aspect of the invention.

According to a fourth aspect, the present invention also encompasses the use of the prepolymer according to the first aspect of the invention or the use of the polyisocyanate composition according to the third aspect of the invention for the preparation of a polyurethane.

According to a fifth aspect, the present invention also encompasses the use of the prepolymer according to the first aspect of the invention, or the use of the polyisocyanate composition according to the third aspect of the invention, as a one component adhesive or as a component in a two component adhesive, preferably wherein the adhesive is a hot melt adhesive or a laminating adhesive.

According to a sixth aspect, the invention encompasses an adhesive comprising the prepolymer according to the first aspect of the invention, or the polyisocyanate composition according to the third aspect of the invention.

According to a seventh aspect, the invention encompasses a one component self leveling liquid membrane prepared from a prepolymer according to the first aspect of the invention, or from a polyisocyanate composition according to the third aspect of the invention.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, which illustrates, by way of example, the principles of the invention.

BRIEF DESCRIPTION OF THE DRAWINGS

FIG. 1 represents the free monomer content vis-a-vis the NCO of the isocyanate-containing compound for the various isocyanate-containing compounds made according to Example 5.

DETAILED DESCRIPTION OF THE INVENTION

Before the present formulations of the invention are described, it is to be understood that this invention is not limited to particular formulations described, since such formulations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise. By way of example, "an isocyanate group" means one isocyanate group or more than one isocyanate groups.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

Throughout this application, the term "about" is used to indicate that a value includes the standard deviation of error for the device or method being employed to determine the value.

As used herein, the terms "% by weight", "wt %", "weight percentage", or "percentage by weight" are used interchangeably.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

According to the first aspect of the present invention, an isocyanate-containing prepolymer is provided, said prepolymer being obtainable by reacting at least one isocyanate with at least one first compound selected from the group comprising monohydric alcohols, thiols and secondary amines; wherein the ratio of the NCO value of the isocyanate-containing prepolymer to the OH, SH or NH value of said monohydric alcohol, thiol or secondary amine respectively ranges from 0.0005 to 1.0000, preferably from 0.0005 to 0.7500, preferably 0.001 to 0.600, said at least one first compound being present in a total amount of at least 40% by weight based on the total weight of the isocyanate-containing prepolymer. Said prepolymer can also be obtainable by mixing at least one isocyanate with at least one first compound selected from the group comprising monohydric alcohols, thiols and secondary amines.

As used herein, the term "isocyanate-containing prepolymer" refers to a prepolymer comprising at least one isocyanate —N=C=O group, whereby the isocyanate group may be a terminating group. Preferably, the isocyanate group is a terminating group. The NCO value (also referred to as percent NCO or NCO content) of the isocyanate-containing prepolymer is preferably measured by titration with dibutylamine according to the DIN 53185 standard. The NCO value is expressed in weight %.

The OH value (also referred to as OH number or OH content) is preferably measured according to the ASTM D 1957 standard. The OH value is expressed in mg KOH/gm. The SH value (also referred to as mercapto value) can be measured by titration with KOH. In brief, SH groups are acetylated with acetic anhydride in the presence of a suitable Lewis base. The excess acetic anhydride is hydrolyzed with water and the resulting acetic acid is titrated with a potassium hydroxide solution. The SH value can then be calculated using the following equation: SH value(mg KOH/g) $=14.025 \times (B-A) \times N/S$ wherein S represents a sample weight (g); A represents the amount (mL) of the solution of potassium hydroxide required for titrating the sample; B represents the amount (mL) of the solution of potassium hydroxide required for a blank test; and N represents the normality of the potassium hydroxide solution.

The NH value can be determined by titration of the sample in ethanol solution with standardized 0.1 N HCl by using bromocresol green solution as an indicator.

When the ratio of the NCO value of the isocyanate-containing prepolymer to the OH, SH or NH value of said monohydric alcohol, thiol or secondary amine respectively ranges from 0.0005 to 1.000, preferably from 0.0005 to 0.7500, it ranges preferably from 0.0010 to 0.6000, preferably from 0.0010 to 0.2000, preferably from 0.0010 to 0.1000, preferably from 0.0010 to 0.0500, preferably from 0.0010 to 0.0200, preferably from 0.0020 to 0.0200, for example from 0.0050 to 0.0200, for example from 0.0100 to 0.0200.

Preferably the NCO value of the prepolymer is at most 15.0%, preferably at most 10.0%, preferably at most 5.0%, preferably at most 2.0%.

Preferably, the first compound is a monohydric alcohol.

As used herein, the terms "monohydric alcohol", "monoalcohol", "mono-ol", or "monol" are synonymous and used interchangeably and refer to an alcohol containing one and only one (1) free hydroxyl (—OH) group.

Non-limiting examples of suitable monohydric alcohols comprise $C_{1-20}$ linear, branched or cyclic hydroxyalkyl containing only one free OH group (also referred as monohydric $C_{1-20}$ hydroxyalkyl); polyesters containing only one free OH group (monohydric polyester), heterocyclyl containing only one free OH group (monohydric heterocyclyl); oxygen containing heterocyclyl containing only one free OH group, and blends thereof. For example, said monohydric alcohol can be a $C_{1-20}$ monohydric hydroxyalkyl, a $C_{2-18}$ monohydric hydroxyalkyl, $C_{3-18}$ monohydric hydroxyalkyl, a $C_{4-18}$ monohydric hydroxyalkyl, a $C_{5-18}$ monohydric hydroxyalkyl, a $C_{6-18}$ monohydric hydroxyalkyl, or a $C_{6-18}$ monohydric hydroxyalkyl. Suitable polyesters comprise compounds containing at least one ester group and bearing at least one pendant alkyl or alkenyl group of at least four carbon atoms, said alkyl or said alkenyl group is substituted with only one free hydroxyl group. Examples of suitable monohydric oxygen containing heterocyclyl are cyclic trimethylolpropane formal and trimethylolpropane oxetane. In a preferred embodiment, the first compound is a monohydric alcohol selected from the group comprising: monohydric polyesters, monohydric $C_{1-20}$ hydroxyalkyl, and monohydric heterocyclyl. Preferably, the monohydric alcohol is a monohydric polyester or a $C_{10-20}$ hydroxyalkyl. Preferably, the monohydric alcohol is a monohydric polyester. In an embodiment, the monohydric alcohol is a $C_{10-20}$ hydroxyalkyl.

The term "alkyl" as a group or part of a group as used herein refers to branched or straight (linear) or cyclic hydrocarbon with no site of unsaturation, preferably having at least 4 carbon atoms in the chain. When a subscript is used herein following a carbon atom, the subscript refers to the number of carbon atoms that the named group may contain. Thus, for example, $C_{1-20}$ alkyl means an alkyl of 1 to 20 carbon atoms.

The term "hydroxyalkyl" and "monohydric hydroxyalkyl" as used herein refers to an alkyl group, as defined above, being substituted with one hydroxyl (—OH) substituent.

The term "alkenyl" as a group or part of a group as used herein refers to a branched or straight or cyclic hydrocarbon with at least one site (usually 1 to 3, preferably 1) of unsaturation, namely a carbon-carbon, sp2 double bond, preferably having at least 4 carbon atoms in the chain. The double bond may be in the cis or trans configuration.

In an embodiment, the first compound is a thiol. As used herein, the term "thiol" refers to compounds comprising at least one free sulfhydryl (—SH) group, preferably one sulfhydryl group. Suitable thiol can be selected from $C_{1-15}$ linear or branched thioalkyl, preferably $C_{2-5}$ linear or branched thioalkyl, or polyesters substituted with one or more thiol groups. Suitable polyesters comprise compounds containing at least one ester group and bearing at least one pendant alkyl or alkenyl group of at least four carbon atoms, said alkyl or said alkenyl group is substituted with at least one thiol group. Suitable thiols can be selected from the group comprising ethanethiol (e-mercaptan), butanethiol (n-butyl mercaptan), tert-butyl mercaptan, and pentanethiols (pentyl mercaptan), such as 1-pentanethiol.

In an embodiment, the first compound is a secondary amine. As used herein, the term "secondary amine" refers to a compound comprising at least one secondary amine group, preferably comprising one and only one (1) secondary amine group. A non-limiting example of a suitable amine is N,N,N',N'-tetramethyldipropylenetriamine (also known as Jeffcat Z-130, commercially available from Huntsman).

Said first compound is present in a total amount of at least 40% by weight based on the total weight of the prepolymer; preferably in an amount of at least 45% by weight, preferably in an amount of at least 50% by weight, preferably in an amount of at least 55% by weight, preferably in an amount of at least 60% by weight, preferably in an amount of at least 65% by weight, preferably in an amount of at least 70% by weight, preferably in an amount of at least 75% by weight, preferably in an amount of at least 80% by weight. In some embodiments, said first compound can be present in a total amount of at least 40% to at most 90% by weight based on the total weight of the prepolymer, preferably in an amount of at least 50% to at most 90%, preferably in an amount of at least 60% to at most 90%, preferably in an amount of at least 70% to at most 90%, preferably in an amount of at least 80% to at most 87%.

By using the first compound in amounts of at least 40 wt % a processable viscosity is obtained and further compatibility as well as stability of the prepolymer is improved.

In an embodiment, said first compound is a monohydric alcohol, and is present in a total amount of at least 40% by weight based on the total weight of the prepolymer; preferably in an amount of at least 45% by weight, preferably in an amount of at least 50% by weight, preferably in an amount of at least 55% by weight, preferably in an amount of at least 60% by weight, preferably in an amount of at least 65% by weight, preferably in an amount of at least 70% by weight, preferably in an amount of at least 75% by weight. In some embodiments, said monohydric alcohol can be present in a total amount of at least 40% to at most 90% by weight based on the total weight of the prepolymer, preferably in an amount of at least 50% to at most 90%.

Preferably, the first compound is a monohydric alcohol having a weight average molecular weight ranging from 32 to 20 000 Da. Preferably, the first compound is a monohydric alcohol having a weight average molecular weight ranging from 100 to 15 000 Da, preferably from 800 to 10 000 Da.

In some embodiments, said first compound comprises at least one tertiary amine group. For example, said first compound can be a monohydric alcohol which comprises at least one tertiary amine group. For example, said monohydric alcohol can be a monohydric polyester substituted with at least one tertiary amine group, a monohydric $C_{1-20}$ hydroxyalkyl substituted with at least one tertiary amine group, or a monohydric heterocyclyl substituted with at least one tertiary amine group. Such tertiary amino groups can be used to increase the blowing and gelling catalytic activity. Preferred compounds comprising a tertiary amine group may be selected from the group comprising: N,N,N'-trimethyl-N'-hydroxyethyl-bisaminoethylether (also known as Jeffcat ZF-10, commercially available from Huntsman), 2-(2-dimethylaminoethoxy)ethanol (also known as DMEE or Jeffcat ZR-70, commercially available from Huntsman), N,N,N'-trimethylaminoethyl-ethanolamine (also known as Jeffcat Z-110, commercially available from Huntsman), N,N-bis(3-dimethylaminopropyl)-N-isopropanolamine (also known as Jeffcat ZR-50, commercially available from Huntsman), and N,N-dimethylethanolamine (also known as DMEA, commercially available from Huntsman).

Optionally, the at least one isocyanate, or the reaction product of the at least one isocyanate with the first compound, can be mixed, preferably subsequently mixed, with at least one second compound selected from the group comprising monohydric alcohols, thiols and secondary amines, wherein said first and second compounds are different. Preferably said at least one isocyanate, or the reaction product of the isocyanate with the first compound, is reacted, preferably subsequently reacted, with at least one second compound, for example at least two, for example at least three compounds selected from the group comprising monohydric alcohols, thiols and secondary amines, wherein said first and further compounds are different. In some embodiments, the mixing and/or reacting steps are performed simultaneously. Preferably, the mixing and/or reacting steps are performed stepwise.

The benefit of adding a further monohydric alcohol, thiol or secondary amine, different from the first one, lies in further reducing the free isocyanate monomer content.

In an embodiment, said at least one isocyanate is mixed and/or reacted with two or more compounds selected from the group comprising monohydric alcohols, thiols and secondary amines, wherein said two or more compounds are different.

Preferably, the at least one second compound is a monohydric alcohol. Said monohydric alcohol can be selected from the group comprising: monohydric polyesters, monohydric $C_{1-20}$ hydroxyalkyl, and monohydric heterocyclyl. Preferably, the at least one second compound is a monohydric alcohol having a weight average molecular weight ranging from 32 to 20 000 Da. Preferably, the at least one second compound is a monohydric alcohol having a weight average molecular weight ranging from 100 to 10 000 Da.

In some embodiments, said second compound has a lower weight average molecular weight than said first compound. In some embodiments, said second compound has a different steric hindrance than said first compound. This can be obtained for example by using different branching structures for the first and second compound.

Preferably, the first compound is a monohydric alcohol, and the second compound is a second monohydric alcohol different from the first one. Said first and second monohydric alcohols can have different weight average molecular weight $M_w$ and/or different OH value. In a preferred embodiment, said second monohydric alcohol has a lower weight average molecular weight than said first monohydric alcohol. In a preferred embodiment, the first and second monohydric alcohols have a different steric hindrance.

In some embodiments, said second compound comprises at least one tertiary amine group. For example, said first compound and/or said at least one second compound can be a monohydric alcohol which comprises at least one tertiary amine group. For example, said monohydric alcohol can be a monohydric polyester substituted with at least one tertiary amine group, a monohydric $C_{1-20}$ hydroxyalkyl substituted with at least one tertiary amine group, or a monohydric heterocyclyl substituted with at least one tertiary amine group. Such tertiary amino groups can be used to increase the blowing and gelling catalytic activity. Preferred compounds comprising a tertiary amine group may be selected from the group comprising: N,N,N'-trimethyl-N'-hydroxyethyl-bisaminoethylether (also known as Jeffcat ZF-10, commercially available from Huntsman), 2-(2-dimethylaminoethoxy)ethanol (also known as DMEE or Jeffcat ZR-70, commercially available from Huntsman), N,N,N'-trimethylaminoethyl-ethanolamine (also known as Jeffcat Z-110, commercially available from Huntsman), N,N-bis(3-dimethylaminopropyl)-N-isopropanolamine (also known as Jeffcat ZR-50, commercially available from Huntsman), and N,N-dimethylethanolamine (also known as DMEA, commercially available from Huntsman).

In some embodiments, said second compound is present in an amount of at least 0.001% by weight based on the total weight of the prepolymer. In some embodiments, said second compound is present in an amount of at least 0.010% by weight based on the total weight of the prepolymer. In some embodiments, said second compound is present in an amount of at least 0.100% by weight based on the total weight of the prepolymer. In some embodiments, said second compound is present in at most 10.0% by weight, preferably in at most 5.0% by weight, preferably in at most 2.0% by weight, preferably in at most 1.0% by weight, preferably in at most 0.5% by weight based on the total weight of the prepolymers. In a preferred embodiment, said second compound is a monohydric alcohol, and is present in an amount of at least 0.001% by weight based on the total weight of the prepolymer. In a preferred embodiment, said second compound is a monohydric alcohol, and is present in an amount of at least 0.010% by weight based on the total weight of the prepolymer. In a preferred embodiment, said second compound is a monohydric alcohol, and is present in an amount of at least 0.100% by weight based on the total weight of the prepolymer. In a preferred embodiment, said second compound is a monohydric alcohol comprising at least one tertiary amine group, and is present in an amount of at least 0.001% by weight based on the total weight of the prepolymer.

In an embodiment, said second compound comprises at least one tertiary amine group and is present in a total amount of at least 0.001% and at most 2.0% by weight based on the total weight of the prepolymer. In an embodiment, said second compound is a monohydric alcohol comprising at least one tertiary amine group and is present in a total amount of at least 0.001% and at most 2.0% by weight based on the total weight of the prepolymer.

In some embodiments, said at least one first compound is present in an amount of at least 40% by weight based on the total weight of the prepolymer, preferably at least 50% by weight, and said second compound is present in an amount of at least 0.001% by weight based on the total weight of the prepolymer.

In some embodiments, said first and second compounds are monohydric alcohols, and said at least one first monohydric alcohol is present in an amount of at least 40% by weight based on the total weight of the prepolymer, preferably at least 50% by weight, and said second monohydric alcohol is present in an amount of at least 0.1% by weight based on the total weight of the prepolymer.

In some embodiments, said first and second compounds are monohydric alcohols, and can be present in a total amount of at least 40.1% by weight based on the total weight of the prepolymer; preferably at least 50.1% by weight, preferably at least 60.1% by weight, and said second monohydric alcohol has a lower weight average molecular weight than said at least one first monohydric alcohol.

In some embodiments, said first and second compounds are monohydric alcohols, said first compound is present in an amount of at least 40% by weight based on the total weight of the prepolymer, said second compound is present in an amount of at least 0.1% by weight based on the total weight of the prepolymer and has a lower weight average molecular weight than said first compound.

In an embodiment, the invention provides the isocyanate-containing prepolymer according to the first aspect of the invention, wherein the ratio of the NCO value of the isocyanate-containing prepolymer, to the weighted average of the OH, SH or NH value, of said first and second compounds respectively ranges from 0.0005 to 1.000, preferably from 0.0005 to 0.7500, for example from 0.0010 to 0.600.

In an embodiment, the invention provides the isocyanate-containing prepolymer according to the first aspect of the invention, wherein the ratio of the NCO value of the isocyanate-containing prepolymer, to the weighted average of the OH, SH or NH values, of all monohydric alcohols, thiols or secondary amines respectively ranges from 0.0005 to 1.000, preferably from 0.0005 to 0.7500, for example from 0.0010 to 0.600.

The weighted average can be calculated as follows. If for example there are 4 parts of a first monol to 3 parts of a second monol, then the weighted average of the OH value is (4×OH value of monol 1+3×OH value of monol 2)/(4+3).

When the ratio of the NCO value of the isocyanate-containing prepolymer to the weighted average of the OH, SH or NH values of two or more monohydric alcohols, thiols or secondary amines respectively ranges from 0.0005 to 1.000, preferably from 0.0005 to 0.7500, it ranges preferably from 0.0010 to 0.6000, preferably from 0.0010 to 0.2000, preferably from 0.0010 to 0.1000, preferably from 0.0010 to 0.0500, preferably from 0.0010 to 0.0200, preferably from 0.0020 to 0.0200, for example from 0.0050 to 0.0200, preferably from 0.0050 to 0.0150.

In some embodiments, the first compound is a polyester containing only one free OH group, preferably a polyester polyol containing only one free OH group, in an amount of at least 40% by weight based on the total weight of the prepolymer. In some embodiments, the first compound can be a monohydric polyester; and the second compound can be a monohydric alcohol selected from monohydric $C_{1-20}$ hydroxyalkyl or blends thereof, and monohydric heterocyclyls. For example, the first compound can be a monohydric polyester present in an amount of at least 40% by weight based on the total weight of the prepolymer; and the second compound can be selected from monohydric $C_{1-20}$ hydroxyalkyl or blends thereof, and monohydric heterocyclyls, and can be present in an amount of at least 0.1% by weight based on the total weight of the prepolymer.

The prepolymer according to the first aspect of the invention comprises at least one isocyanate. Preferably, the at least one isocyanate comprises a methylene diphenyl diisocyanate. In a preferred embodiment, the methylene diphenyl diisocyanate has a functionality of at least 2.0, preferably at least 2.2, more preferably at least 2.4, more preferably at least 2.6, more preferably at least 2.8. As used herein, the term "functionality" refers to the average number of isocyanate groups per molecule, averaged over a statistically relevant number of molecules present in the isocyanate.

In an embodiment the at least one isocyanate comprises polymeric methylene diphenyl diisocyanate which can be any mixture of pure MDI (2,4'-, 2,2'- and 4,4'-methylene diphenyl diisocyanate) and higher homologues of formula (I):

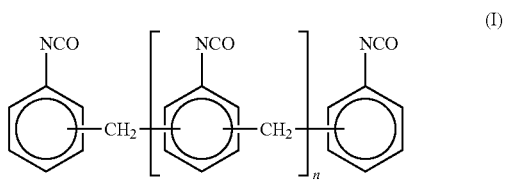

wherein n is an integer which can be from 1 to 10, preferably from 1 to 5.

In an embodiment, the at least one isocyanate is present in an amount of at least 15% by weight, preferably at least 20% by weight, preferably at least 25% by weight, preferably at least 30% by weight based on the total weight of the prepolymer.

The at least one isocyanate may also comprise another polyisocyanate. Preferably the polyisocyanate comprises a high functionality polymeric polyisocyanate, with a functionality of at least 2.8, preferably at least 2.9, preferably at least 3.0. Non-limiting examples of polyisocyanates which may be used in the prepolymer of the present invention include aliphatic isocyanates such as hexamethylene diisocyanate; m- and p-phenylene diisocyanate, tolylene-2,4- and tolylene-2,6-diisocyanate (also known as toluene diisocyanate, and referred to as TDI, such as 2,4-TDI and 2,6-TDI) in any suitable isomer mixture, chlorophenylene-2,4-diisocyanate, naphthylene-1,5-diisocyanate, diphenylene-4,4'-diisocyanate, 4,4'-diisocyanate-3,3'-dimethyl-diphenyl, 3-methyl-diphenylmethane-4,4'-diisocyanate and diphenyl ether diisocyanate; and cycloaliphatic diisocyanates such as cyclohexane-2,4- and -2,3-diisocyanate, 1-methylcyclohexyl-2,4- and -2,6-diisocyanate and mixtures thereof and bis-(isocyanatocyclohexyl)methane (e.g. 4,4'-diisocyanatodicyclohexylmethane (H12MDI)), triisocyanates such as 2,4,6-triisocyanatotoluene and 2,4,4-triisocyanatodiphenylether, isophorone diisocyanate (IPDI), butylene diisocyanate, trimethylhexamethylene diisocyanate, isocyanatomethyl-1,8-octane diisocyanate, tetramethylxylene diisocyanate (TMXDI), 1,4-cyclohexanediisocyanate (CDI), and tolidine diisocyanate (TODI).

The present inventors have found that the prepolymer according to the first aspect of the invention can have an improved processability, due to low viscosity. This effect was even observed without the need of a plasticizer.

Preferably, the viscosity is measured before addition of a plasticizer or a viscosity reducer, herein referred to as a "non-plasticized prepolymer". In a preferred embodiment, the viscosity of the (non-plasticized) prepolymer ranges from 1000 to 200 000 mPa·s, for example from 1500 to 150 000 mPa·s, for example from 2000 to 100 000 mPa·s, for example from 2500 to 50 000 mPa·s, for example from 5000 to 20 000 mPa·s, for example from 5000 to 18 000 mPa·s, for example from 5000 to 15 000 mPa·s, wherein the viscosity is measured at 25° C. using Brookfield Viscometer (model DV-II, spindle 21, rpm according 30-80% of full scale) according to the ASTM D 4889 standard without any plasticizer added to the prepolymer.

The present inventors have also found that the prepolymer can have a reduced content in free isocyanate monomers, such as methylene diphenyl diisocyanate monomers in the form of 2,4', 2,2' and 4,4' isomers and mixtures thereof.

In some embodiments, the prepolymer according to the first aspect of the invention comprises at most 10% by weight of free isocyanate monomers, preferably at most 5.0% by weight of free isocyanate monomers, preferably at most 3.0% by weight of free monomers, preferably at most 2.0% by weight of free monomers, preferably at most 1.0% by weight of free monomers, preferably at most 0.5% by weight of free monomers, most preferably at most 0.1% by weight of free monomers, with % by weight based on 100% by the total weight of the prepolymer. Preferably, the free isocyanate monomer content is measured before addition of a plasticizer or a viscosity reducer. Preferably, the free isocyanate monomer content is measured by quantitative HPLC GC analysis.

The prepolymer may comprise one or more additives. In some embodiments, the additive is present in an amount of at least 0.01% by weight, for example at least 0.03% by weight, for example at least 0.1% by weight, preferably at least 0.3% by weight, for example at least 0.5%, for example at least 1.0% by weight, based on the total weight of the prepolymer.

The additive may be a plasticizer. Preferably, the amount of plasticizer in the prepolymer is limited. In a preferred embodiment, the prepolymer comprises from 0.0% to at most 50.0% by weight of plasticizer, preferably from 0.0% to at most 15.0% by weight of plasticizer, preferably from 0.0% to at most 10.0% by weight of plasticizer, preferably from 0.0% to at most 5.0% by weight of plasticizer, preferably from 0.0% to at most 1.0% by weight of plasticizer, preferably from 0.00% to at most 0.01% by weight of plasticizer, preferably from 0.000% to at most 0.001% by weight of plasticizer, based on the total weight of the prepolymer.

Suitable plasticizers, for purposes of the present invention, comprise conventional plasticizers known in the art, such as esters of dibasic or polybasic carboxylic acids with monohydric alcohols. Non-limiting examples of such polycarboxylic acids may be selected from the group comprising succinic acid, isophthalic acid, trimellitic acid, phthalic acid anhydride, tetrahydrophthalic acid anhydride, hexahydrophthalic acid anhydride, endomethylene-tetrahydrophthalic acid anhydride, glutaric acid anhydride, maleic acid anhydride, fumaric acid and dimeric and trimeric fatty acids (such as oleic acid), and combinations thereof, which may be mixed with monomeric fatty acids. Suitable monohydric alcohols are as described and exemplified above.

Other examples of suitable plasticizers may be selected from the group comprising phthalates, such as dioctyl phthalate, diisooctyl phthalate, diisononyl phthalate, dimethyl phthalate, dibutyl phthalate; phosphates, such as tributyl phosphate, triethyl phosphate (TEP), triphenyl phosphate and cresyl diphenyl phosphate; chlorinated biphenyls; aromatic oils; adipates, such as diisononyl adipate and di-(2-ethylhexyl) adipate; and combinations thereof. Specific examples of suitable plasticizers are commercially available from the BASF Corporation under the trademark of PALATINOL®, such as PALATINOL® 711P, and under the trademark of PLASTOMOLL®, such as PLASTOMOLL® DNA and PLASTOMOLL® DOA.

Other examples of suitable plasticizers, comprise phosphoric acid esters of the above-mentioned branched and unbranched aliphatic, cycloaliphatic and aromatic alcohols. If appropriate, phosphates of halogenated alcohols, for example, trichloroethyl phosphate, can also be employed. It is to be appreciated that mixed esters of the aforementioned alcohols and carboxylic acids can also be employed. So called polymeric plasticizers can also be employed, for purposes of the present invention. Examples of such plasticizers may be selected from the group comprising polyesters of adipic acid, sebacic acid or phthalic acid. Phenol alkylsulfonates, e.g. phenyl paraffinsulfonates, can also be employed. It is to be appreciated that the prepolymer may comprise any combination of two or more of the aforementioned plasticizers. Alternatively, such plasticizers may also be selected from alkylene carbonates, such as propylene carbonate and ethylene carbonate. These are commercially available from Huntsman under the Jeffsol® trademark.

The additive may be an amine. In a preferred embodiment the prepolymer comprises at least one amine. Preferably, the amine is a secondary amine, for example dibutylamine.

According to the second aspect of the invention, a process for preparing an isocyanate-containing prepolymer according to the first aspect of the invention is provided, comprising the step of:

(a) reacting at least one isocyanate with at least one first compound selected from the group comprising monohydric alcohols, thiols and secondary amines; wherein the ratio of the NCO value of the isocyanate-containing prepolymer to the OH, SH or NH value of said monohydric alcohol, thiol or secondary amine respectively ranges from 0.0005 to 1.000, preferably from 0.0005 to 0.7500, preferably ranges from 0.001 to 0.600 and wherein said at least one first compound is present in a total amount of at least 40% by weight based on the total weight of the isocyanate-containing prepolymer; thereby preparing an isocyanate-containing prepolymer. In some embodiments, the at least one isocyanate comprises a methylene diphenyl diisocyanate.

According to some embodiments, the method further comprises the step of:

(b) optionally reacting the at least one isocyanate and/or the product of step (a) with at least one second compound selected from the group comprising monohydric alcohols, thiols and secondary amines, wherein said second compound is different from said first compound.

In some embodiments, the process according to the second aspect can further comprise the step of:

(b) subsequently reacting the at least one isocyanate and/or the product of step (a) with two or more second compounds selected from the group comprising monohydric alcohols, thiols and secondary amines, wherein said second compounds are different from said first compound.

In some embodiments, the process according to the second aspect can further comprise the steps of:

(b) reacting the at least one isocyanate and/or the product of step (a) with at least one second compound selected from the group comprising monohydric alcohols, thiols and secondary amines, wherein said second compound is different from said first compound; and (c) reacting the at least one isocyanate and/or the product of step (a) and/or (b) with at least one third compound selected from the group comprising monohydric alcohols, thiols and secondary amines, wherein said third compound is different from said first compound and said second compound.

In a preferred embodiment, at least one mixing/reacting step is performed at a temperature of at least 60° C., preferably at least 65° C., preferably at least 70° C., preferably at least 75° C., preferably at least 80° C. Preferably, all mixing/reacting steps are performed at said temperature.

The compounds, such as the monohydric alcohols, may be gradually added to the at least one isocyanate, for example step wise, or they may be continuously added, for example drop by drop. Preferably, the compounds are added continuously drop by drop. Preferably, the monohydric alcohols are continuously added drop by drop.

In some embodiments, at least one mixing/reacting step can be performed in the presence of a catalyst. All mixing/reacting steps can also be performed in the presence of a catalyst.

Non-limiting examples of suitable catalysts include non grafted catalysts, such as 2,2'-dimorpholinodiethylether (DMDEE, available commercially from Huntsman), and grafted catalysts, such as dimethylethanolamine (DMEA) and 2(2-dimethylaminoethoxy)ethanol (DMEE). Preferably, the catalyst is 2,2'-dimorpholinodiethylether (DMDEE) or 2(2-dimethylaminoethoxy)ethanol (DMEE). Preferably, the catalyst is a grafted catalyst.

In some embodiments, the catalyst is an organometallic catalyst. In these embodiments, the catalyst comprises an element selected from the group comprising tin, iron, lead, bismuth, mercury, titanium, hafnium, zirconium, and combinations thereof. In certain embodiments, the catalyst comprises a tin catalyst. Suitable tin catalysts, for purposes of the present invention, may be selected from tin(II) salts of organic carboxylic acids, e.g. tin(II) acetate, tin(II) octoate, tin(II) ethylhexanoate and tin(II) laurate. In an embodiment, the organometallic catalyst comprises dibutyltin dilaurate, which is a dialkyltin(IV) salt of an organic carboxylic acid. Specific examples of suitable organometallic catalyst, e.g. dibutyltin dilaurates, for purposes of the present invention, are commercially available from Air Products and Chemicals, Inc. under the trademark of DABCO®. The organometallic catalyst can also comprise other dialkyltin(IV) salts of organic carboxylic acids, such as dibutyltin diacetate, dibutyltin maleate and dioctyltin diacetate.

Non-limiting examples of other suitable catalysts, may be selected from the group comprising iron(II) chloride; zinc chloride; lead octoate; tris(dialkylaminoalkyl)-s-hexahydrotriazines including tris(N,N-dimethylaminopropyl)-s-hexahydrotriazine; tetraalkylammonium hydroxides including tetramethylammonium hydroxide; alkali metal hydroxides including sodium hydroxide and potassium hydroxide; alkali metal alkoxides including sodium methoxide and potassium isopropoxide; and alkali metal salts of long-chain fatty acids having from 10 to 20 carbon atoms and/or lateral OH groups; triethylamine, N,N,N',N'-tetramethylethylenediamine, N,N-dimethylaminopropylamine, N,N,N',N',N"-pentamethyldipropylenetriamine, tris(dimethylaminopropyl)amine, N,N-dimethylpiperazine, tetramethylimino-bis (propylamine), dimethylbenzylamine, trimethyl amine, triethanolamine, N,N-diethyl ethanolamine, N-methylpyrrolidone, N-methylmorpholine, N-ethylmorpholine, bis(2-dimethylamino-ethyl)ether, N,N-dimethylcyclohexylamine (DMCHA), N,N,N',N',N"-pentamethyldiethylenetriamine, 1,2-dimethylimidazole, 3-(dimethylamino) propylimidazole; N,N,N-dimethylaminopropylhexahydrotriazine, potassium acetate, N,N,N-trimethyl isopropyl amine formate, and combinations thereof. It is to be appreciated that the catalyst component may include any combination of two or more of the aforementioned catalysts.

Preferably, the catalyst is present in an amount of at least 10 ppm, preferably at least 0.01% by weight, preferably at least 0.20% by weight, with % by weight based on the total weight of the prepolymer.

According to a third aspect, the invention encompasses a polyisocyanate composition comprising the isocyanate-containing prepolymer according to the first aspect of the invention.

The invention encompasses the use of the prepolymer according to the first aspect of the invention or the polyisocyanate composition according to the third aspect of the invention for the preparation of an adhesive, a coating, an elastomer, a foam, or a polyurethane. The invention also encompasses said prepared adhesive, coating, elastomer, foam or polyurethane.

According to a fourth aspect, the present invention also encompasses the use of the prepolymer according to the first aspect of the invention or the use of the polyisocyanate composition according to the third aspect of the invention for the preparation of a polyurethane. The invention also encompasses said polyurethane.

The invention encompasses the use of the prepolymer in a one-component system, which can be cured by moisture. The invention also encompasses said one-component system. The invention also encompasses the use of the prepolymer in a two-component system, preferably in a two-component polyurethane or a two-component heat curable polyisocyanurate system. The invention also encompasses said two-component system.

According to a fifth aspect, the present invention also encompasses the use of the prepolymer according to the first aspect of the invention, or the use of the polyisocyanate composition according to the third aspect of the invention, as a one component adhesive or as a component in a two component adhesive. The invention also encompasses said one component adhesive or said two component adhesive. Preferably these adhesives are used for laminating an object.

According to a sixth aspect, the invention encompasses an adhesive comprising the prepolymer according to the first aspect of the invention, or the polyisocyanate composition according to the third aspect of the invention.

The prepolymers according to the invention or the polyisocyanates obtained therewith are particularly useful as raw material for formulating a one-component (1C), for example moisture curing, adhesive, with free monomer content of at most 1.0 weight %, preferably at most 0.5 weight %, preferably at most 0.2 weight %, most preferably at most 0.1 weight %. The prepolymers according to the invention or the polyisocyanates obtained therewith are also particularly useful for formulating a two-component (2C) adhesive, with free monomer content of at most 1.0 weight %, preferably at most 0.5 weight %, preferably at most 0.2 weight %, most preferably at most 0.1 weight %.

A one-component adhesive may comprise DIY (do-it-yourself) adhesives, which react with moisture in the air. A two-component system may react with a polyol. Preferably, the adhesive is a D4 adhesive. As used herein, the term D4 adhesive refers to adhesives corresponding to the EN 204 specifications for the D4 class. In some embodiments of the invention, the prepolymer fulfills the D4 (EN 204) specifications for DIY wood adhesives, while showing a free monomer content of at most 1.0 weight %, preferably at most 0.5 weight %, preferably at most 0.2 weight %, most preferably at most 0.1 weight %.

Preferably, the adhesive is a hot melt adhesive. The invention also encompasses said hot melt adhesive. The prepolymers according to the invention or the polyisocyanates obtained therewith are particularly useful for formulating a reactive hot melt (RHM) adhesive, with free monomer content of at most 1.0 weight %, preferably at most 0.5 weight %, preferably at most 0.2 weight %, most preferably at most 0.1 weight %.

Preferably, the adhesive is a laminating adhesive. The invention also encompasses said laminating adhesive. The prepolymers according to the invention or the polyisocyanates obtained therewith are particularly useful for formulating a laminating adhesive, with free monomer content of at most 1.0 weight %, preferably at most 0.5 weight %, preferably at most 0.2 weight %, most preferably at most 0.1 weight %.

In some embodiments, the prepolymer can be particularly useful for formulating a laminating adhesive, and preferably for flexible packaging adhesive. The prepolymers are particularly useful as raw material for formulating fast curing and low migration 1C and 2C flexible packaging adhesives.

Preferably, the laminating adhesive is a 2C system. Some adhesives according to embodiments of the present invention provide bonds suitable to be used in flexible packaging for indirect food contact, due to a reduced migration of aromatic amines, i.e. a migration rate below the legally required limit, for example below a content of 2 ppb of polyaromatic amine.

In some embodiments, two-components systems based on these prepolymers, can achieve permanent tack properties. Accordingly, the present invention also encompasses pressure sensitive adhesive prepared using the prepolymers according to the invention.

The prepolymer is particularly useful for flexible packaging where a laminated film or sheet, produced using an adhesive, is used.

As an applicator of an adhesive according to the present invention there can be mentioned known applicators such as airless spray machine, air spray machine, immersion, roll coater, brush and the like. The conditions used for lamination using an adhesive according to the invention are preferably 20 to 150° C., for example 20 to 100° C., for example 40 to 150° C., particularly preferably 40 to 100° C.

In producing a laminated film by using the present adhesive, the film used is not critical. As the film, there can be mentioned a film of polyester type such as polyethylene terephthalate or the like; a film of polyolefin type such as polyethylene, polypropylene or the like; a film of polyamide type such as nylon or the like; a metal foil such as aluminum foil, copper foil or the like; an ethylene-vinyl acetate copolymer or a saponification product thereof; a cellophane; a polyvinyl chloride; a polyvinylidene chloride; a polystyrene; a paper; and so forth. There can also be suitably used stretched products thereof and surface-treated (e.g. corona discharge-treated or surface-coated) products thereof.

The adhesive of the present invention can be suitably used for lamination not only between two film layers but also between three or more film layers.

The prepolymers according to the invention or the polyisocyanates obtained therewith are particularly useful as raw material for formulating a one-component moisture curing self leveling liquid membrane for coating applications. According to a seventh aspect, the invention encompasses a one component self leveling liquid membrane prepared from a prepolymer according to the first aspect of the invention, or from a polyisocyanate composition according to the third aspect of the invention.

In some embodiments, the prepolymer can be useful for formulating an adhesive for a material comprising lignocellulose, herein also referred to as a "lignocellulosic material".

The present invention also encompasses a substrate comprising a prepolymer according to the invention. The present invention also encompasses a lignocellulosic body prepared using the prepolymer according to the invention.

The invention also encompasses the use of the prepolymer for the preparation of a coating, an elastomer, a one component foam, or a two component foam.

The invention is illustrated but not limited by the following examples.

EXAMPLES

The examples described hereunder illustrate the properties of the prepolymers and compositions according to embodiments of the present invention. Unless otherwise indicated, all parts and all percentages in the following examples, as well as throughout the specification, are parts by weight or percentages by weight respectively.

The following ingredients were used in the preparation of the prepolymers:

Isocyanate 1: polymeric methylene diphenyl isocyanate (pMDI), with an NCO value of 31.0%, with a functionality of 2.7 (softblock content 0.0%).

Isocyanate 2: polymeric methylene diphenyl isocyanate (pMDI) of NCO value 30.5%, with a functionality of 2.85 (softblock content 0.0%).

Monol 1: polyester monol of $M_w$ 900, and a functionality of 1, based on transesterification and dehydration reaction products of castor oil with glycerol.

Monol 2: blend of $C_{12}$-$C_{13}$ primary alcohols of $M_w$ 193, and a functionality of 1, CAS no 67762-41-8, available as Neodol 23E from Shell Chemicals.

Monol 3: CTPF (cyclic trimethylol propane formal) also known as 5-ethyl-1,3-dioxane-5-methanol, CAS no 5187-23-5 with $M_w$ 146.

Monol 4: TMPO (trimethylol propane oxetane) also known as 3-ethyl-3-oxetanemethanol, CAS no 3047-32-3 with $M_w$ 116.

Monol 5: Glycerin Carbonate, Jeffsol GC available from Huntsman

Thiol 1: pentanethiol.

Secondary amine 1: N,N,N',N'-tetramethyldipropylenetriamine, commercially available from Huntsman as Jeffcat Z-130.

Diol 1: polypropylene glycol of molecular weight 2000 (PPG2000).

Diol 2: polypropylene glycol of functionality 2 and molecular weight of 125.

DMDEE: 2,2'-dimorpholinodiethylether.

DMEA: N,N-dimethylethanolamine.

Methods

The following methods were used in the examples:

The NCO value (or percent NCO), given in weight %, was measured according to the DIN 53185 standard. In brief, isocyanate is reacted with an excess of di-n-butylamine to form ureas. The unreacted amine is then titrated with standard nitric acid to the color change of bromocresol green indicator or to a potentiometric endpoint. The percent NCO or NCO-value is defined as the percent by weight of NCO-groups present in the product.

The OH value (also referred to as OH number or OH content) was measured according to the ASTM D 1957 standard. In brief, hydroxyl groups are acetylated with acetic anhydride in the presence of pyridine and heat. The excess acetic anhydride is hydrolyzed with water and the resulting acetic acid is titrated with standard potassium hydroxide solution. The OH value is expressed in mg KOH/g sample. The OH value was calculated using the following equation:

OH value(mg KOH/g)=56.1×(B−A)×N/S wherein S represents a sample weight (g); A represents the amount (mL) of the solution of potassium hydroxide required for titrating the sample; B represents the amount (mL) of the solution of potassium hydroxide required for a blank test; and N represents the normality of the potassium hydroxide solution.

The concentration in free monomer was measured by quantitative HPLC GC analysis.

Final lap shear strength in climate condition (after 7 days at 23° C. 50% RH), after boiling (a boiling test of 6 hr and after this condition 2 hr cold water) and after water immersion (4 days in water at 20° C.+/−5° C.) of the prepolymers was determined according to Standard EN 204-205.

Example 1

The prepolymers (Prepo.) 1-4 were prepared by mixing monol 1, having an OH value of 62, with isocyanate 2. The formulations are listed in Table 1. The comparative prepolymers (Comp. prepo) 1-4 were obtained by mixing diol 1 having an OH value of 56, with isocyanate 2. The formulations are listed in Table 1.

The NCO value (NCO value in prepo) and the free monomer content of the prepolymers were measured. The ratio NCO value of the prepolymer to the OH value of the monol or diol (NCO prepo/OH alcohol) was determined. The results are listed in Table 1.

The viscosity of the obtained prepolymers was determined and their stability visually assessed.

The durability of some prepolymers (1, 6 and 10) was further tested according to EN-204-205.

After 7 days (final strength) in climate condition (23° C. 50% RH) a lap shear strength was measured. After the final strength was reached, a lap shear strength (water test) was measured after 4 days in water (20+/−5° C.). The final strength also resisted a boiling test of 6 hr and after this condition 2 hr cold water. The lap shear measured after the boiling test is also shown in Table 3.

The prepolymers 1, 6 and 10 achieved the D4 classification.

TABLE 3

| | Final strength (MPa) | Boiling Test (MPa) | Water Test (MPa) | NCO value in prepo (wt %) | Free isocyanate monomer (wt %) |
|---|---|---|---|---|---|
| Prepo 1 | 10.6 | 5.2 | 4.9 | 15 | 17.9 |
| Prepo 6 | 11.2 | 4.5 | 5.1 | 10 | 0.5 |
| Prepo 10 | 10.8 | 4.1 | 4.8 | 4.7 | 0.4 |

TABLE 1

| | Isocyanate 2 (wt %) | Monol 1 (wt %) | Diol 1 (wt %) | NCO value in prepo | NCO prepo/ OH alcohol | Free isocyanate (wt %) | Viscosity/ Wetting mPas @ 25° C. | Appearance at 25° C. | Appearance at 80° C. | Stability 24 hr @ 80° C. |
|---|---|---|---|---|---|---|---|---|---|---|
| Prepo 1 | 55.89 | 44.11 | 0.00 | 15 | 0.2419 | 17.9 | 2500 | Clear | Clear | Okay |
| Comp. prepo 1 | 55.32 | 0.00 | 44.68 | 15 | 0.2679 | 19.3 | 16000 | Clear | Clear | Okay |
| Prepo 2 | 41.66 | 58.34 | 0.00 | 10 | 0.1613 | 10.0 | 3600 | Clear | Clear | Okay |
| Comp. prepo 2 | 40.91 | 0.00 | 59.09 | 10 | 0.1786 | 14.2 | 34000 | Clear | Milky | Phase separating |
| Prepo 3 | 27.44 | 72.56 | 0.00 | 5 | 0.0806 | 2.1 | 11000 | Clear | Clear | Okay |
| Comp. prepo 3 | 26.50 | 0.00 | 73.50 | 5 | 0.0893 | 8.5 | 228000 | Milky | Phase separating | Phase separating |
| Prepo 4 | 15.00 | 85.00 | 0.00 | 1 | 0.0161 | <0.1 | 43000 | Clear | Clear | Okay |
| Comp. prepo 4 | 15.97 | 0.00 | 84.03 | 1 | 0.0179 | 2.4 | | Milky | Phase separating | Gelled |

The prepolymers 5-11 were prepared by mixing monol 1, having an OH value of 62, monol 2, having an OH value of 290, monol 3, having an OH value of 390, monol 4, having an OH value of 475, or monol 5, having an OH value of 475, with isocyanate 1 or 2. The formulations are listed in Table 2.

The NCO value and the free monomer content of the prepolymers (prepo) were measured. The ratios of the NCO value of the prepolymer to the OH value of the monol (NCO prepo/OH) are listed in Table 2.

Example 2

The prepolymers 12 to 17 were prepared by mixing the ingredients of prepolymer 3 of example 1 with DMDEE, DMEA, or secondary amine 1 as shown in Table 4. The free monomer content and the NCO value of the prepolymers were measured and compared with the free monomer content of prepolymer 3. The results are listed in Table 4.

TABLE 2

| | Isocyanate 1 (wt %) | Isocyanate 2 (wt %) | Monol 1 (wt %) | Monol 2 (wt %) | Monol 3 (wt %) | Monol 4 (wt %) | Monol 5 (wt %) | NCO value in prepo (wt %) | NCO prepo/OH | Free isocyanate monomer (wt %) |
|---|---|---|---|---|---|---|---|---|---|---|
| Prepo 5 | 16.00 | 0.00 | 84.00 | 0.00 | 0.00 | 0.00 | 0.00 | 1 | 0.0161 | 0.5 |
| Prepo 6 | 0.00 | 60.00 | 0.00 | 40.00 | 0.00 | 0.00 | 0.00 | 10 | 0.0345 | 0.5 |
| Prepo 7 | 0.00 | 51.00 | 0.00 | 49.00 | 0.00 | 0.00 | 0.00 | 5 | 0.0172 | <0.1 |
| Prepo 8 | 43.40 | 0.00 | 0.00 | 56.60 | 0.00 | 0.00 | 0.00 | 1 | 0.0034 | <0.1 |
| Prepo 9 | 57.00 | 0.00 | 0.00 | 0.00 | 43.00 | 0.00 | 0.00 | 5 | 0.0105 | 0.3 |
| Prepo 10 | 60.00 | 0.00 | 0.00 | 0.00 | 0.00 | 40.00 | 0.00 | 4.7 | 0.0099 | 0.4 |
| Prepo 11 | 55.15 | 0.00 | 0.00 | 0.00 | 0.00 | 0.00 | 44.84 | 1 | 0.0021 | 0.2 |

TABLE 4

| | Prepo 3 (wt %) | DMDEE (wt %) | DMEA (wt %) | Secondary amine 1 (wt %) | Free isocyanate monomer (wt %) | NCO value in prepo (wt %) |
|---|---|---|---|---|---|---|
| Prepo 3 | 100.0 | 0.0 | 0.0 | 0.0 | 2.1 | 5 |
| Prepo 12 | 99.9 | 0.1 | 0.0 | 0.0 | 1.7 | 5 |
| Prepo 13 | 99.8 | 0.2 | 0.0 | 0.0 | 1.2 | 4.9 |
| Prepo 14 | 99.7 | 0.3 | 0.0 | 0.0 | 0.9 | 4.8 |
| Prepo 15 | 99.0 | 1.0 | 0.0 | 0.0 | 0.8 | 4.4 |
| Prepo 16 | 98.2 | 0.0 | 1.8 | 0.0 | 0.9 | 4 |
| Prepo 17 | 93.0 | 0.0 | 0.0 | 7.0 | <0.1 | 3 |

Example 3

The prepolymers 18 and 19 were prepared by mixing secondary amine 1 with isocyanate 2. The NCO value of the prepolymers was measured. The formulations and NCO values are listed in Table 5.

TABLE 5

| | Isocyanate 2 (wt %) | Secondary amine 1 (wt %) | NCO value in prepo (wt %) |
|---|---|---|---|
| Prepo 18 | 60.0 | 40.0 | 9.3 |
| Prepo 19 | 51.8 | 48.2 | 5 |

Example 4

The prepolymers 20 and 21 were prepared by mixing thiol 1 with isocyanate 2. The NCO value of the prepolymers was measured. The formulations and NCO values are listed in Table 6.

TABLE 6

| | Isocyanate 2 (wt %) | Thiol 1 (wt %) | NCO value in prepo (wt %) | Free isocyanate monomer (wt %) |
|---|---|---|---|---|
| Prepo 20 | 59.9 | 40.1 | 2.5 | |
| Prepo 21 | 57.8 | 42.2 | 1 | <0.1 |

Example 5

The prepolymers 22 to 33 were prepared by mixing either two diols or one or two monols with isocyanate 2. The NCO value of the prepolymers was measured. The formulations and NCO values are listed in Table 7.

TABLE 7

| | Isocyanate 2 | Monol 1 | Monol 2 | Diol 1 | Diol 2 | NCO value in prepo | NCO prepo/OH alcohol(s) | Free isocyanate monomer |
|---|---|---|---|---|---|---|---|---|
| Prepo 22 | 59.8 | 32.16 | 8.04 | 0.00 | 0.00 | 15 | 0.1349 | 10.9 |
| Prepo 23 (comp) | 67.22 | 0.00 | 0.00 | 26.22 | 6.56 | 15 | 0.0669 | 17.5 |
| Prepo 24 | 55.89 | 44.11 | 0.00 | 0.00 | 0.00 | 15 | 0.2419 | 17.9 |
| Prepo 25 | 46.83 | 42.54 | 10.63 | 0.00 | 0.00 | 10 | 0.0929 | 6.1 |
| Prepo 26 (comp) | 56.65 | 0.00 | 0.00 | 34.68 | 8.67 | 10 | 0.0446 | 11.3 |
| Prepo 27 | 41.66 | 58.34 | 0.00 | 0.00 | 0.00 | 10 | 0.1613 | 10 |
| Prepo 28 | 33.86 | 52.91 | 13.23 | 0.00 | 0.00 | 5 | 0.04645 | 1.3 |
| Prepo 29 (comp) | 46.07 | 0.00 | 0.00 | 43.13 | 10.79 | 5 | 0.0223 | 5.9 |
| Prepo 30 | 27.44 | 72.56 | 0.00 | 0.00 | 0.00 | 5 | 0.0806 | 2.1 |
| Prepo 31 | 23.49 | 61.21 | 15.3 | 0.00 | 0.00 | 1 | 0.0093 | 0.05 |
| Prepo 32 (comp) | 37.61 | 0.00 | 0.00 | 49.91 | 12.48 | 1 | 0.0045 | 1.4 |
| Prepo 33 | 15.00 | 85.00 | 0.00 | 0.00 | 0.00 | 1 | 0.0161 | 0.05 |

FIG. 1 represents the free monomer content vis-a-vis the NCO of the prepolymer for the various prepolymers above made either with two diols, two monols or one monol.

It is clear that especially at low NCO values using one monol leads to a decrease in free monomer content over using two diols and that using two monols leads to an even further decrease.

It is to be understood that although preferred embodiments have been discussed for providing embodiments according to the present invention, various modifications or changes may be made without departing from the scope and spirit of this invention.

The invention claimed is:

1. An isocyanate-containing prepolymer obtained by reacting at least one polyisocyanate with at least one first compound selected from the group consisting of monohydric alcohols, monohydric thiols and monohydric secondary amines; wherein the ratio of the NCO value of the isocyanate-containing prepolymer to the OH, SH or NH value of said monohydric alcohol, monohydric thiol or monohydric secondary amine ranges from 0.0005:1 to 1.0000:1 and wherein said at least one first compound is present in a total amount of at least 40% by weight based on the total weight of the isocyanate-containing prepolymer.

2. The isocyanate-containing prepolymer according to claim 1, wherein said first compound is a monohydric alcohol selected from the group consisting of monohydric polyesters, monohydric C1-20 hydroxyalkyl, and monohydric heterocyclyl.

3. The isocyanate-containing prepolymer according to claim 1, wherein the viscosity of the isocyanate-containing prepolymer ranges from 1000 to 200 000 mPa·s, wherein the viscosity is measured at 25° C. using Brookfield Viscometer according to the ASTM D 4889 standard without any plasticizer added to the isocyanate-containing prepolymer.

4. The isocyanate-containing prepolymer according to claim 1, wherein the at least one polyisocyanate comprises a methylene diphenyl diisocyanate.

5. The isocyanate-containing prepolymer according to claim 1, wherein the reaction product of the at least one polyisocyanate with the first compound, is reacted with at least one second compound selected from the group consisting of monohydric alcohols, monohydric thiols and monohydric secondary amines, and wherein said first and second compounds are different.

6. The isocyanate-containing prepolymer according to claim 5, wherein said at least one second compound has a lower weight average molecular weight than said at least one first compound and/or wherein said at least one second compound has a different steric hindrance than said first compound.

7. The isocyanate-containing prepolymer according to claim 1, wherein the isocyanate-containing prepolymer has a free isocyanate monomer content of at most 1.0 wt %, based on the total weight of the isocyanate-containing prepolymer as measured by quantitative HPLC GC analysis.

8. The isocyanate-containing prepolymer according to claim 1, wherein the at least one polyisocyanate comprises a polymeric methylene diphenyl diisocyanate.

9. A process for preparing an isocyanate-containing prepolymer as defined in claim 1, comprising the step of:
reacting at least one polyisocyanate with at least one first compound selected from the group consisting of monohydric alcohols, monohydric thiols and monohydric secondary amines; wherein the ratio of the NCO value of the isocyanate-containing prepolymer to the OH, SH or NH value of said monohydric alcohol, monohydric thiol or monohydric secondary amine ranges from 0.0005:1 to 1.0000:1 and wherein said at least one first compound is present in a total amount of at least 40% by weight based on the total weight of the isocyanate-containing prepolymer; thereby preparing the isocyanate-containing prepolymer.

10. A polyisocyanate composition comprising the isocyanate-containing prepolymer as defined in claim 1.

11. An adhesive comprising the isocyanate-containing prepolymer as defined in claim 1 or the polyisocyanate composition as defined in claim 10.

12. A one component self leveling liquid membrane prepared from an isocyanate-containing prepolymer as defined in claim 1, or from a polyisocyanate composition as defined in claim 10.

* * * * *